Figure 1:
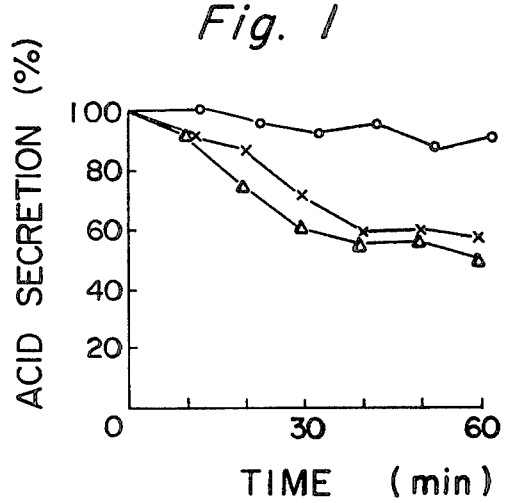

United States Patent [19]

Shiratsuchi et al.

[11] 4,216,225

[45] Aug. 5, 1980

[54] METHYLMETHIONINESULFONIUM COMPOUNDS, PROCESS FOR THEIR PREPARATION, AND PHARMACEUTICAL COMPOSITIONS CONTAINING THEM

[75] Inventors: Masami Shiratsuchi, Musashimurayama; Kiyoshi Kawamura, Higashimurayama; Hisashi Kunieda, Higashimurayama; Naoki Machida, Higashimurayama; Toshihiro Akashi, Higashimurayama; Masahiko Nagakura, Sayama, all of Japan

[73] Assignee: Kowa Company, Ltd., Japan

[21] Appl. No.: 906,567

[22] Filed: May 16, 1978

[30] Foreign Application Priority Data

May 18, 1977 [JP] Japan ................ 52-56310

[51] Int. Cl.$^2$ .................... A61K 31/55; A61K 31/215
[52] U.S. Cl. ................... 424/287; 424/263; 424/319; 424/309; 260/558 S; 260/448 R; 546/316; 546/323; 546/335; 560/16; 562/426; 546/336; 546/337; 546/334
[58] Field of Search ................ 260/558 S, 448 R; 560/16; 562/426; 424/324, 287, 309, 319

[56] References Cited

FOREIGN PATENT DOCUMENTS 48-76857  3/1973  Japan .
6514139  2/1966  Netherlands .

OTHER PUBLICATIONS

Hawkins et al., "Biochem. J.," vol. 104, pp. 762–766 (1967).
Mizsak et al., "J. Org. Chem.," vol. 31, pp. 1964–1965 (1966).
Sugano et al., "Bull. Chem. Soc. Japan," vol. 46, pp. 669–670 (1973).

*Primary Examiner*—Henry R. Jiles
*Assistant Examiner*—Robert T. Bond
*Attorney, Agent, or Firm*—Wenderoth, Lind & Ponack

[57] ABSTRACT

Methylmethioninesulfonium compounds of the formula $$\begin{array}{c} H_3C \\ \phantom{H_3C}\diagdown \\ \phantom{H_3C}\phantom{\diagdown}S^{\oplus}-CH_2CH_2-CH-R^2 \\ \phantom{H_3C}\diagup \phantom{XXXXXXXXXX} | \\ H_3C \phantom{\diagup} X^{\ominus} \phantom{XXXXX} NH-R^1 \end{array}$$

wherein
  $X^{\ominus}$ represents an anion;
  $R^1$ represents a hydrogen atom or an acyl group of the formula -$COR^3$ in which $R^3$ represents an alkyl group with 1 to 20 carbon atoms, the group —$(CH_2)_2$ COOH or the group $$-Z-\!\!\!\left\langle\begin{array}{c}\phantom{X}\\=Y\end{array}\!\!\!\right\rangle\!\!-(R^4)_n$$

in which Z represents a direct bond or a methylene or vinylene linkage, Y represents C or N, $R^4$ represents a member selected from the class consisting of a hydrogen atom, lower alkyl groups, lower alkoxy groups, di-lower-alkylamino groups and a sulfamoyl group, n is a number of 1 to 3, and two or more $R^4$ groups may be identical or different; and
  $R^2$ represents the group —$COOR^5$ in which $R^5$ represents a hydrogen atom, an alkyl group with 1 to 5 carbon atoms or a metal- or metal complex-forming moiety, or the group $$-CON\!\!\begin{array}{c}\diagup R^6\\ \diagdown R^6\end{array}$$

in which $R^6$ groups may be identical or different, and each represent a hydrogen atom or an alkyl group with 1 to 5 carbon atoms, with the proviso that when $R^1$ represents a hydrogen atom, $R^2$ is not —COOH; when $R^1$ represents a hydrogen atom and $R^2$ represents —CONH$_2$, X$^\ominus$ is not Cl$^\ominus$; and when R$^1$ is —COCH$_3$ and R$^2$ is —COOCH$_3$, X$^\ominus$ is not I$^\ominus$.

The compounds can be easily prepared from methionine as a starting material by a combination of known unit reactions such as methylsulfonium-forming reaction, acylation, amidation, esterification and metal salt-forming reaction. These compounds are especially useful for treating ulcers.

15 Claims, 4 Drawing Figures

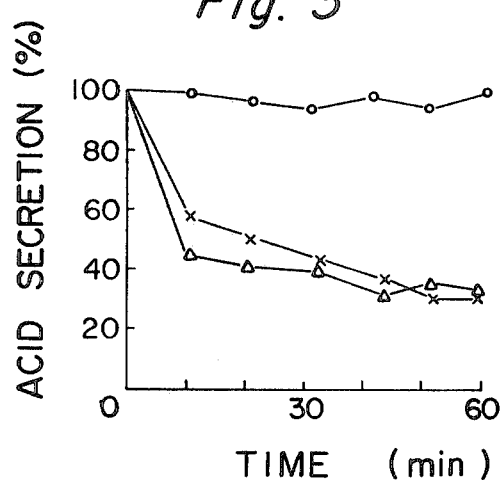
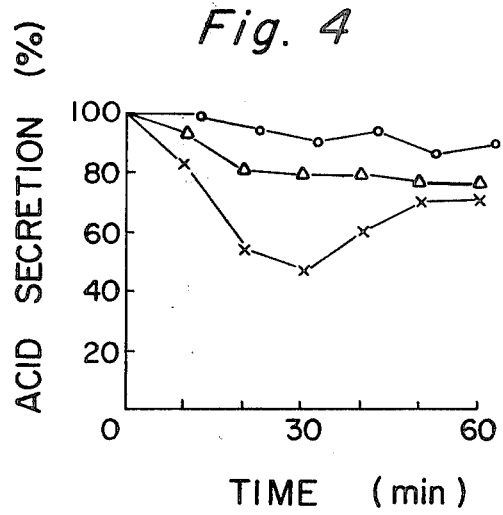

METHYLMETHIONINESULFONIUM COMPOUNDS, PROCESS FOR THEIR PREPARATION, AND PHARMACEUTICAL COMPOSITIONS CONTAINING THEM

This invention relates to methylmethioninesulfonium compounds not described heretofore in the literature, a process for their preparation, and pharmaceutical compositions, especially ulcer-treating agents containing them.

More specifically, the invention relates to methylmethioninesulfonium compounds of the following formula

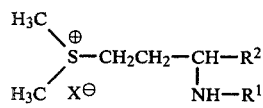

wherein
X$^\ominus$ represents an anion; R$^1$ represents a hydrogen atom or an acyl group of the formula —COR$^3$ in which R$^3$ represents an alkyl group with 1 to 20 carbon atoms, the group —(CH$_2$)$_2$COOH or to the group

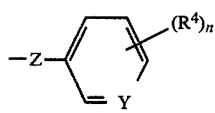

in which Z represents a direct bond or a methylene or vinylene linkage, Y represents C or N, R$^4$ represents a member selected from the class consisting of a hydrogen atom, lower alkyl groups, lower alkoxy groups, di-lower-alkylamino groups and a sulfamoyl group, n is a number of 1 to 3, and two or more R$^4$ groups may be identical or different; and R$^2$ represents the group —COOR$^5$ in which R$^5$ represents a hydrogen atom, an alkyl group with 1 to 5 carbon atoms or a metal- or metal complex-forming moeity, or the group

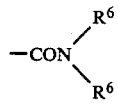

in which R$^6$ groups may be identical or different, and each represent a hydrogen atom or an alkyl group with 1 to 5 carbon atoms, with the proviso that when R$^1$ represents a hydrogen atom,, R$^2$ is not —COOH; when R$^1$ represents a hydrogen atom and R$^2$ represents —CONH$_2$, X$^\ominus$ is not Cl$^\ominus$; and when R$^1$ is —COCH$_3$ and R$^2$ is —COOCH$_3$, X$^\ominus$ is not I$^\ominus$.

The present invention also relates to a process for preparing these methylmethioninesulfonium compounds.

The invention also relates to ulcer treating agents comprising such a methylmethioninesulfonium compound as an active ingredient, which is especially useful for the therapy and prophylaxis of ulcers in the digestive organs such as gastric ulcer and duodenal ulcer.

Methylmethioninesulfonium halides of the following formula

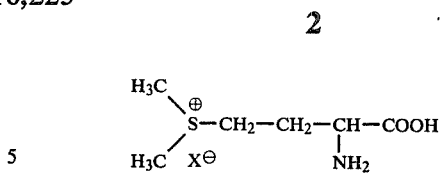

wherein X$^\ominus$ represents an anion, espcially Cl$^\ominus$ and Br$^\ominus$ have previously been known, and it is also known that the compounds of formula (A) are useful as ulcer-treating agents (California Med. 77, 248–252[1952]).

Methylmethioninamidesulfonium chloride of the following formula

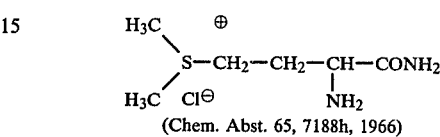

(Chem. Abst. 65, 7188h, 1966)

and N-acetyl-methylmethioninesulfonium iodide, methyl ester of the following formula

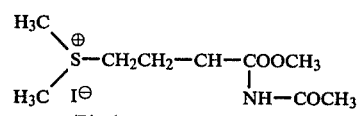

(Biochem. J., 104, 762, 1967)

are known as analogous compounds. The compound of formula (C) has been reported with regard to its interaction with chemotrypsin, and the compound of formula (B), as an intermediate for the preparation of a thiadiazole.

The present inventors have made investigations on methylmethioninesulfonium halide derivatives, and found that the methylmethioninesulfonium compounds of formula (I) which are not described in the literature can be prepared in good yields by an easy operation.

It has also been found that these novel compounds have superior prophylactic and therapeutic effects as ulcer-treating agents and exhibit low toxicity, and that a preferred group of compounds within formula (I) show a better treating effect than the known compound of formula (A).

It is an object of this invention therefore to provide methylmethioninesulfonium compounds not described heretofore in the literature.

Another object of this invention is to provide a process for preparing the compunds of formula (I) with commercial advantages.

Still another object of this invention relates to a pharmaceutical composition, especially an ulcer treating composition, comprising a compound of formula (I) as an active ingredient.

The above and other objects and advantages of the invention will become more apparent from the following description.

The novel methylmethioninesulfonium compounds of this invention are expressed by the following formula (I):

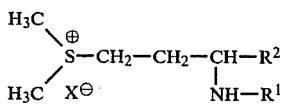

wherein all symbols are as defined hereinabove.

Examples of the anion represented by $X^-$ are anions derived from halides, sulfuric acid, hyposulfurous acid, phosphoric acid, nitric acid, and dialkylsulfates. Preferred anions are, for example, $CH_3SO_4^{\ominus}$, $C_2H_5SO_4^{\ominus}$, $SO_4^{2\ominus}$, $HSO_4^{\ominus}$, $Cl^{\ominus}$, $Br^{\ominus}$, and $I^{\ominus}$. The halogen anions are especially preferred.

In formula (I), $R^1$ represents a hydrogen atom and an acyl group of the formula $-COR^3$. $R^3$ is a member selected from the class consisting of alkyl groups with 1 to 20 carbon atoms, the group; $-(CH_2)_2COOH$, and the group

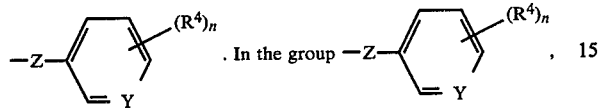

. In the group

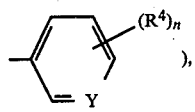

Z represents a direct bond (therefore, $R^3$ is the group

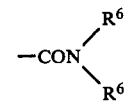

), or represents a methylene or vinylene linkage. Y represents C or N. $R^4$ represents a member of the class consisting of a hydrogen atom, lower alkyl groups such as alkyl groups containing 1 to 3 carbon atoms, lower alkoxy groups such as alkoxy groups containing 1 to 3 carbon atoms, di-lower-alkylamino groups such as di($C_1$-$C_3$ alkyl)amino groups and a sulfamoyl group. n is a positive number of 1 to 3, and when there are two or more $R^4$ groups, they may be identical or different.

Examples of the alkyl group represented by $R^3$ are methyl, ethyl, n-propyl, iso-propyl, n-butyl, iso-butyl, t-butyl, n-pentyl, n-hexyl, heptyl, octyl, decyl, undecyl, dodecyl, tridecyl, tetradecyl, pentadecyl, hexadecyl, heptadecyl, octadecyl, nonadecyl, and eicosyl.

Specific examples of the acyl group $-COR^3$ thus include acetyl, propionyl, n-butylryl, iso-butyryl, pivaloyl, n-pentyl (valeryl), isovaleryl, n-hexanoyl, pentanoyl, octanoyl, decanoyl, undecanoyl, dodecanoyl (lauroyl), tridecanoyl, tetradecanoyl (myristoyl), petadecanoyl, hexadecanoyl (palmitoyl), heptadecanoyl, octadecanoyl (stearoyl), nonadecanoyl, eicosanoyl, carboxyacetyl, carboxypropionyl, carboxybutyryl, carboxyvaleryl, benzoyl, 2-, 3- or 4-methylbenzoyl, 2-methoxybenzoyl, 3-methoxybenzoyl, 4-methoxybenzoyl, 3,4,5-trimethoxybenzoyl, 2-methoxy-5-sulfamoyl benzoyl, 2-, 3- or 4-dimethylaminobenzoyl, 2-, 3- or 4-butylaminobenzoyl, nicotinoyl, iso-nicotinoyl, cinnamoyl, and phenylacetyl.

$R^2$ in formula (I) represents the group $-COOR^5$ in which $R^5$ represents a hydrogen atom, an alkyl group with 1 to 5 carbon atoms, or a metal- or metal complex-forming moiety; or $$-CON\begin{matrix}R^6\\R^6\end{matrix}$$

in which $R^6$ groups may be identical or different, and each represent a hydrogen atom or an alkyl group with 1 to 5 carbon atoms.

Examples of the alkyl groups $R^5$ and $R^6$ are the same as those of $C_1$-$C_5$ alkyl groups exemplified hereinabove with regard to $R^3$. An example of the metal complex-forming moiety is $Al_3(OH)_4$ which can be expressed as

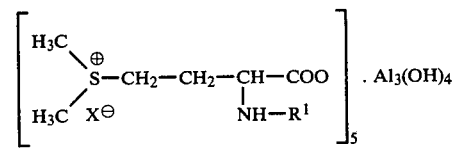

Examples of the metal are Na, K, Ca and Mg.

Typical examples of the compound of formula (I) are shown in Table 1. The physico-chemical properties of these compounds are shown in Examples to be given hereinbelow Table 1

| Compound No. | $R^1$ | $R^2$ | $X^{\ominus}$ | salt |
|---|---|---|---|---|
| 1 | $-COC_2H_5$ | $-COOH$ | Cl | |
| 2 | $-COC_7H_{15}$ | $-COOH$ | Cl | |
| 3 | 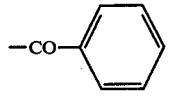 | $-COOH$ | Cl | |
| 4 | $-COCH_3$ | $-COOH$ | Cl | |
| 5 | $-COC_3H_7$ | $-COOH$ | Cl | |
| 6 | $-COC_3H_7(iso)$ | $-COOH$ | Cl | |
| 7 | $-COC_5H_{11}$ | $-COOH$ | Cl | |
| 8 | $-COC_9H_{19}$ | $-COOH$ | Cl | |
| 9 | $-COC_{11}H_{23}$ | $-COOH$ | Cl | |
| 10 | $-COC_{13}H_{27}$ | $-COOH$ | Cl | |
| 11 | $-COC_{17}H_{35}$ | $-COOH$ | Cl | |
| 12 | $-CO(CH_2)_2COOH$ | $-COOH$ | Cl | |
| 13 | 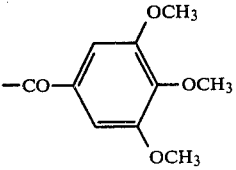 | $-COOH$ | | |

Table 1-continued

| Compound No. | R¹ | R² | X⊖ | salt |
|---|---|---|---|---|
| 14 | —CO—C₆H₄—OCH₃ (para) | —COOH | Cl | |
| 15 | —CO—C₆H₄—OCH₃ (ortho) | —COOH | Cl | |
| 16 | —CO—C₆H₃(OCH₃)(SO₂NH₂) (with H₃CO) | —COOH | Cl | |
| 17 | —CO—C₆H₄—CH₃ | —COOH | Cl | |
| 18 | —CO—C₆H₄—N(CH₃)₂ | —COOH | Cl | |
| 19 | —CO—(pyridyl) | —COOH | Cl | |
| 20 | —CO—CH₂—C₆H₅ | —COOH | HSO₄ | |
| 21 | —CO—CH=CH—C₆H₅ | —COOH | Cl | |
| 22 | H | —COOC₂H₂ | Cl | HCl salt |
| 23 | H | —COOCH₃ | Cl | HCl salt |
| 24 | H | —COOC₄H₉ | Cl | HCl salt |
| 25 | —COCH₃ | —COOCH₃ | Cl | |
| 26 | —COCH₃ | —COOC₂H₅ | Cl | |
| 27 | —COCH₃ | —COOC₃H₇ | Cl | |
| 28 | —COCH₃ | —COOC₄H₉ | Cl | |
| 29 | —COC₇H₁₅ | —COOCH₃ | Cl | |
| 30 | —COC₇H₁₅ | —COOC₂H₅ | Cl | |
| 31 | —COC₇H₁₅ | —COOC₃H₇ | Cl | |
| 32 | H | —CONHC₂H₅ | Cl | |
| 33 | H | —CONHC₄H₉ | Cl | |
| 34 | —COCH₃ | —CONH₂ | Cl | |
| 35 | —COC₇H₁₅ | —CONH₂ | Cl | |
| 36 | —COCH₃ | —COO . 1/5Al₃(OH)₄ | Cl | |
| 37 | —COC₂H₅ | " | Cl | |
| 38 | —COC₃H₇ | —COO . 1/5Al₃(OH)₄ | Cl | |
| 39 | —COC₃H₇(iso) | " | Cl | |
| 40 | —COC₅H₁₁ | " | Cl | |
| 41 | —COC₉H₁₉ | " | Cl | |
| 42 | —CO—C₆H₅ | " | Cl | |

The compounds of formula (I) can be easily prepared from methionine as a starting material by a combination of known unit reactions such as methylsulfonium-forming reaction, acylation, esterification, amidation and metal salt-forming reaction. For an easy understanding, the manufacturing process is schematically shown below. In the following scheme, abbreviations (Ia) to (If) have the following meanings.

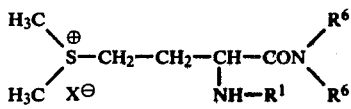

(Ia)

wherein $X^\ominus$ and $R^6$ are as defined with regard to formula (I), and $R_1$ represents an acyl group of the formula $-COR^3$ represented by $R^1$ in formula (I).

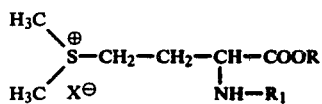

(Ib)

wherein $X^\ominus$ represents an anion which when $R_1$ is $-COCH_3$ and R is $CH_3$, is not $I^\ominus$, $R_1$ represents an acyl group of the formula $-COR^3$ represented by $R^1$ in formula (I), and R represents a $C_1$-$C_5$ alkyl group represented by $R^5$ in formula (I).

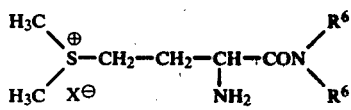

(Ic)

wherein $X^\ominus$ is an anion excepting $Cl^\ominus$, and $R^6$ is as defined with regard to formula (I).

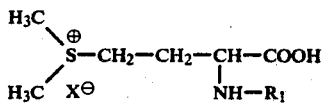

(Id)

wherein $X^\ominus$ is the same as defined with regard to formula (I), and $R_1$ represents an acyl group of the formula $-COR^3$ represented by $R^1$ in formula (I).

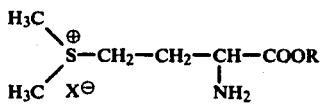

(Ie)

wherein $X^\ominus$ is as defined in formula (I), and R represents an alkyl group with 1 to 5 carbon atoms represented by $R^5$ in formula (I).

$$\begin{array}{c} H_3C \\ \phantom{H_3}\diagdown_{\oplus} \\ \phantom{H_3C\diagdown}S-CH_2-CH_2-CH-COOM \\ \phantom{H_3}\diagup \phantom{XXXXXXXXX} | \\ H_3C \phantom{X} X^\ominus \phantom{XXXXX} NH-R^1 \end{array}$$

(If)

wherein $X^\ominus$ and $R^1$ are as defined with regard to formula (I), and M represents a metal- or metal complex-forming moiety.

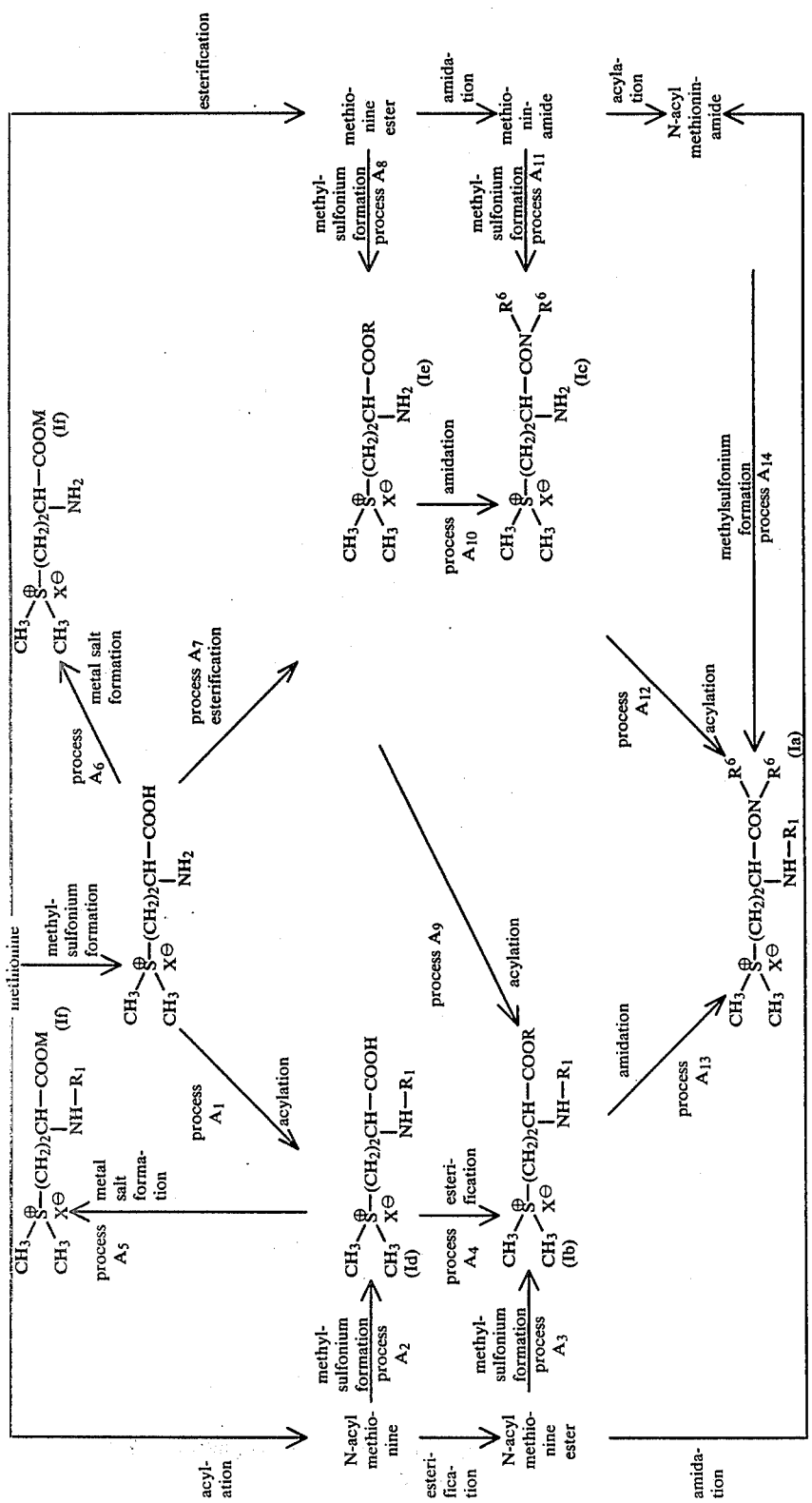

The process for preparing the compounds of this invention shown in the above flowsheet is summarized as follows:

Process A₁

A process for preparing a methylmethioninesulfonium compound of the following formula

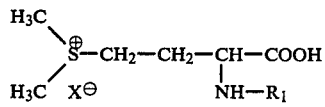

wherein X⁻ represents an anion, R₁ represents an acyl group of the formula —COR³ in which R³ is as defined with regard to formula (I), which comprises acylating a methylmethioninesulfonium compound of the formula

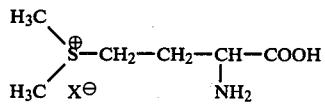

wherein X⁻ is as defined.

Process A₂

A process for preparing a methylmethioninesulfonium compound of the formula

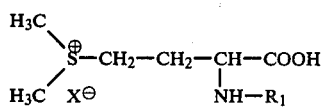

wherein X⁻ represents an anion, and R₁ represents an acyl group of the formula —COR³ in which R³ is as defined with regard to formula (I), which comprises converting an N-acylmethionine of the formula

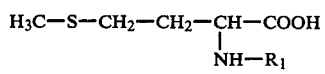

wherein R₁ is as defined, into a methylsulfonium compound.

Process A₃

A process for preparing a methylmethioninesulfonium compound expressed by the formula

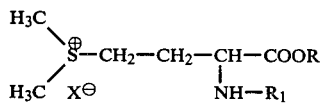

wherein X⁶³ represents an anion, R represents an alkyl with 1 to 5 carbon atoms, and R₁ represents an acyl group of the formula —COR³ in which R³ is as defined with regard to formula (I), with the proviso that when R₁ is —COCH₃ and R is methyl, X⁻ is not I⁻, which comprises converting an N-acylmethionine ester of the formula

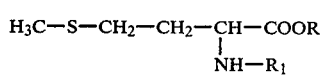

wherein R₁ and R are as defined, into a methylsulfonium compound.

Process A₄

A process for preparing a methylmethioninesulfonium compound of the formula

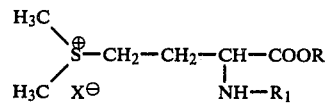

wherein X⁻ represents an anion, R₁ represents an acyl group of the formula —COR³ in which R³ is as defined with regard to formula (I), and R represents an alkyl group with 1 to 5 carbon atoms with the proviso that when R₁ is —COCH₃ and R is methyl, X⁻ is not I⁻, which comprises esterifying a methylmethioninesulfonium compound of the formula

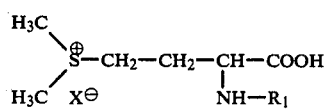

wherein X⁻ and R₁ are as defined.

Process A₅

A process for preparing a methylmethioninesulfonium compound of the formula

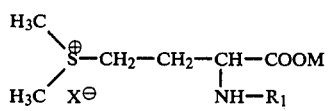

wherein X⁻ represents an anion, R₁ represents an acyl group of the formula —COR³ in which R³ is as defined in formula (I), and M represents a metal- or metal complex-forming moiety, which comprises converting a methylmethioninesulfonium compound of the formula

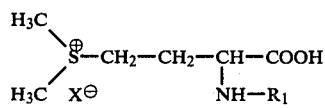

wherein X⁻ and R₁ are as defined, into a metal salt.

Process A₆

A process for preparing a methylmethioninesulfonium compound of the formula

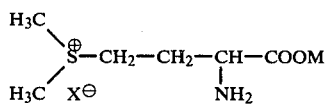

wherein X⁻ represents an anion, and M represents a metal or metal complex-forming moiety, which comprises converting a methylmethioninesulfonium compound of the formula

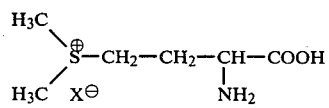

wherein X⁻ is as defined, into a metal salt.

Process A₇

A process for preparing a methylmethioninesulfonium compound expressed by the formula

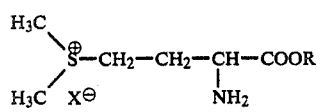

wherein $X^{\ominus}$ represents an anion, and R represents a alkyl group with 1 to 5 carbon atoms, which comprises esterifying a methylmethioninesulfonium compound of the formula

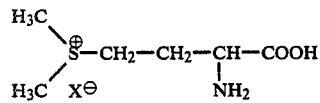

wherein $X^{\ominus}$ is as defined.

Process $A_8$

A process for preparing a methylmethioninesulfonium compound expressed by the following formula

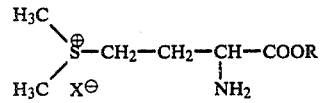

wherein $X^{\ominus}$ represents an anion and R represents an alkyl group with 1 to 5 carbon atoms, which comprises converting a methionine ester of the formula

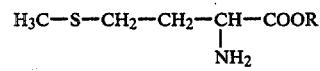

wherein R is as defined, into a methylsulfonium compound.

Process $A_9$

A process for preparing a methylmethioninesulfornium compound of the formula

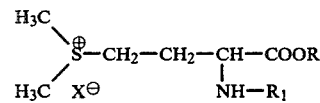

wherein $X^{\ominus}$ represents an anion, R represents an alkyl group with 1 to 5 carbon atoms, and $R_1$ represents an acyl group of the formula $-COR^3$ in which $R^3$ is as defined with regard to formula (I), which comprises acylating a methylmethioninesulfonium compound of the formula

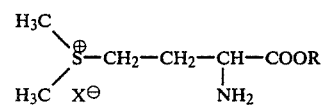

wherein $X^{\ominus}$ and R are as defined.

Process $A_{10}$

A process for preparing a methylmethioninesulfonium compound expressed by the following formula

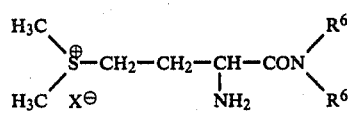

wherein $X^{\ominus}$ represents an anion, and $R^6$ is as defined with regard to formula (I), with the proviso that when two $R^6$ groups are hydrogen, $X^{\ominus}$ is not $Cl^{\ominus}$, which comprises amidating a methylmethioninesulfonium compound of the formula

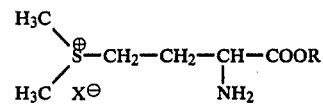

wherein $X^-$ is as defined, and R represents an alkyl group with 1 to 5 carbon atoms.

Process $A_{11}$

A process for preparing a methylmethioninesulfonium compound expressed by the formula

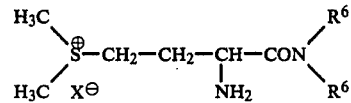

wherein $X^{\ominus}$ represents an anion, and $R^6$ is as defined with regard to formula (I), with proviso that when two $R^6$ groups are hydrogen, $X^{\ominus}$ is not $Cl^{\ominus}$, which comprises converting a methioninamide of the formula

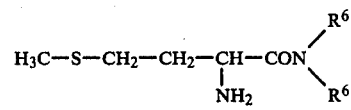

wherein $R^6$ is as defined, into a methylsulfonium compound.

Process $A_{12}$

A process for preparing a methylmethioninesulfonium compound of the formula

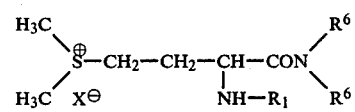

wherein $X^{\ominus}$ represents an anion, $R^6$ is as defined above with regard to formula (I) with the proviso that when two $R^6$ groups are hydrogen atoms, $X^{\ominus}$ is not $Cl^{\ominus}$, and $R_1$ represents an acyl group of the formula $-COR^3$ in which $R^3$ is as defined with regard to formula (I), which comprises acylating a methylmethioninesulfonium compound of the formula

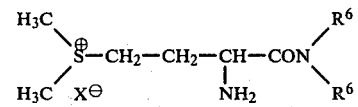

wherein $X^{\ominus}$ and $R^6$ are as defined above.

Process $A_{13}$

A process for preparing a methylmethioninesulfonium compound expressed by the following formula

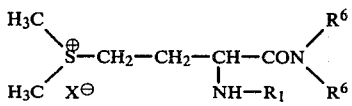

wherein $X^\ominus$ represents an anion, $R_1$ represents an acyl group of the formula $-COR^3$ in which $R^3$ is as defined with regard to formula (I), and $R^6$ is as defined with regard to formula (I), which comprises amidating a methylmethioninesulfonium compound of the formula

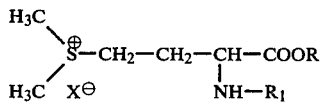

wherein $X^\ominus$ and $R_1$ are as defined, and R represents an alkyl group with 1 to 5 carbon atoms.

Process $A_{14}$

A process for preparing a methylmethioninesulfonium compound of the formula

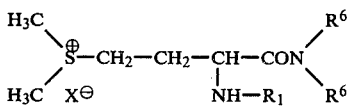

wherein $X^-$ represents an anion, $R_1$ represents an acyl group of the formula $-COR^3$ in which $R^3$ is as defined with regard to formula (I), and $R^6$ is as defined with regard to formula (I), which comprises converting an N-acylmethioninamide of the formula

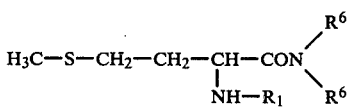

wherein $R_1$ and $R^6$ are as defined, into a methylsulfonium compound.

The unit reactions shown in Processes $A_1$ to $A_{14}$ above, such as methylsulfonium formation, acyltion, esterification, amidation and metal salt formation, are known, and each of them can be performed under the same conditions in different combinations of such unit reactions.

The reaction conditions for each unit reaction are described below.

The methylsulfonium-forming reaction can be performed by treating the starting methionine or an intermediate derived from it with a methylating agent. The reaction can be performed in the absence or presence of a solvent. The reaction can be performed at a temperature of about 0° to 100° C. The reaction time is, for example, about 30 minutes to about 10 hours. The methylating agent can be used in a stoichiometrical amount, but preferably its amount is from an equivalent to 10 moles per mole of the starting material. Examples of the methylating agent are dimethyl sulfate, methyl halides especially methyl iodide, and methanol/sulfuric acid. Examples of the reaction solvent include water, methanol, ethanol, tetrahydrofuran, dioxane, acetone, acetic acid, and mixed solvents of water with these organic solvents.

When the anion $X^\ominus$ of the reaction product formed by the methylsulfonium-forming reaction is desired to be converted to another anion $X^\ominus$, the product may be converted to the form of sulfonium hydroxide by using an OH-type ion exchange resin, and then reacted with a suitable compound capable of giving the desired anion $X^\ominus$. For example, hydrochloric acid is used when it is desired to convert the anion into $Cl^\ominus$.

The acylation can be performed by treating the starting methionine, an intermediate derived from it, or a compound of formula (I) in which $R^1$ is hydrogen with an acylating agent. The reaction is carried out preferably in a solvent. The reaction temperature is, for example, from about 10° to the reflux temperature. The reaction can be carried out by using a stoichiometrical amount of the acylating agent, and preferably from about an equivalent to about 5 moles per mole of the starting material, of the acylating agent can be used. The reaction can be performed, for example, for several hours to several days. Examples of the acylating agent are acid halides and acid anhydrides. Suitable solvents include, for example, methanol, ethanol, acetone, tetrahydrofuran, dioxane, acetic acid, carboxylic acids corresponding to the acylating agents, an aqueous solution of an alkali hydroxide, especially an aqueous solution of sodium hydroxide.

In the present invention, the esterification reaction can be performed by treating the starting methionine, an intermediate derived from it or a compound of formula (I) in which $R^2$ is a carboxyl group, with an alcohol, for example. Desirably, the reaction is carried out in the presence of a dehydrating agent. Preferably, the reaction is carried out under mild reaction conditions. The reaction temperature is, for example, about $-10°$ to 100° C. The reaction time is about 1 to 24 hours. The reaction can be performed in the presence or absence of a solvent. Examples of the dehydrating agent are hydrochloric acid, sulfuric acid, p-toluenesulfonic acid, and thionyl chloride.

Suitable solvents include acetone, tetrahydrofuran, dioxane, methanol, ethanol, n-butanol, n-propanol and other alcohols corresponding to the esters The amidation can be carried out by treating a methionine ester, an N-acylmethionine ester or a compound of formula (I) in which $R^2$ is $-COO$-alkyl, with an amidating agent, for example. The reaction can be performed preferably in the presence of a solvent. Since the reaction proceeds at room temperature, cooling or heating is not specifically necessary. For example, the reaction temperature is about 0° to about 50° C. The reaction time is about 1 to 7 days. If the amidating agent is liquid under the reaction conditions, it is possible to use the amidating agent in excess to cause it to serve also as a solvent. A compound of formula (I) in which $R^2$ is $-COOH$ can also be amidated, but it is preferred to perform the reaction after the compound has been converted to an ester. The reaction can be performed by using a stoichiometrical amount of the amidating agent, but preferably its amount is from about an equivalent to about 10 moles per mole of the starting material.

The amidating agent includes, for example, ammonia, and alkylamines having a $C_1$-$C_5$ alkyl group such as ethylamine or butylamine. Examples of the solvent are water, methanol, ethanol, tetrahydrofuran, and dioxane. Liquid amidating agents can also be used as solvent.

The metal salt-forming reaction can be performed by contacting a compound (Id) shown in the above flow-sheet in which $R^2$ is —COOH or a methylmethioninesulfonium halide with a metal salt-forming metal-containing compound. The reaction can be performed in the presence of a solvent. The reaction temperature is, for example, about 0° to about 50° C., and the reaction time is, for example, about 1 to about 10 hours.

Preferred metal compounds used to form the metal salt are metal alcoholates. Examples of the metal alcoholates are lower alcoholates (such as methylate, ethylate or propylate) of metals such as sodium, potassium, calcium, aluminum and magnesium. Examples of suitable solvents are water, tetrahydrofuran, dioxane, and alcoholate-forming alcohols such as methanol, ethanol, isopropanol and butanol.

The amount of the metal lower alcoholate can be varied as desired, and is about an equivalent per mole of the metal salt-forming compound.

The novel compounds of formula (I) of this invention exhibit useful pharmacological effects, for example an antiulcer activity useful for the prophylaxis and therapy of ulcers, and an anti-allergic activity useful for the treatment of allergic diseases. They also show an activity of increasing the blood flow in the gastric wall, and the various other activities shown experimentally hereinbelow. These compounds are especially useful as treating agents for various ulcers, such as gastric ulcer, duodenal ulcer, gastritis, dermatic ulcer, and hyperacidity.

Thus, according to this invention, there is provided an ulcer treating agent comprising a compound of formula (I) as an active ingredient.

There can also be provided an ulcer treating composition composed of an anti-ulceratively effective amount of a compound of formula (I) and a pharmaceutically acceptable diluent or carrier.

In the ulcer treating agent or composition of this invention, the compound of formula (I) is preferably a compound of the following formula

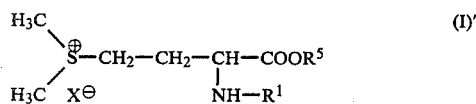

(I)' wherein $X^\ominus$, $R^1$ and $R^5$ are as defined with regard to formula (I), and when $R^1$ is hydrogen, $R^5$ is not hydrogen and when $R^1$ is —COCH$_3$ and $R^5$ is methyl, $X^\ominus$ is not $I^\ominus$. More preferably, the compound of formula (I) is a compound of the following formula

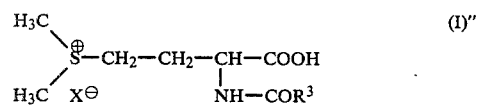

(I)'' wherein $X^\ominus$ and $R^3$ are as defined with regard to formula (I'').

In the formula (II''), $R^3$ especially preferably represents an alkyl group containing 1 to 20 carbon atoms, especially 1 to 10 carbon atoms, or the group

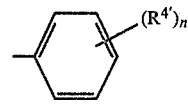

in which $R^{4'}$ represents a member selected from the class consisting of a hydrogen atom, lower alkyl groups such as $C_1$–$C_4$ alkyl groups and lower alkoxy groups such as $C_1$–$C_4$ alkoxy groups, and n is a positive number of 1 to 3, preferably a positive number of 1 to 2.

In the ulcer treating agent or composition of this invention, the active ingredient may be one or more of the compounds of formula (I). The active ingredient in accordance with this invention may be administered alone or in conjunction with a pharmaceutically acceptable diluent or carrier in any desired dosage forms.

Examples of the diluent or carrier are solid diluents or carries such as corn starch, wheat starch, potato starch, lactose, sucrose, glucose, mannitol, calcium sulfate, calcium phosphate, calcium carbonate, sodium chloride, boric acid, dextrin, gum aragic, tragacanth gum, carrageenan, sodium alginate, gelatin, methyl cellulose, ethyl celululose, carboxymethyl cellulose, hydroxyethyl cellulose, hydroxyethyl starch, hydroxypropyl cellulose, polyvinylpyrrolidine, polyvinyl alcohol, magnesium stearate, talc, aluminum silicate, boric acid, and magnesium oxide, and liquid diluents or carriers such as a physiologival saline solution, distilled water for injection, and an aqueous solution of glucose.

The ulcer treating agent of this invention is preferably in an orally administrable form such as a tablet, capsule, granule and powder. In parenteral administration (e.g., intramuscular or intravenous), it may be in the form of a sterilized liquid such as a solution or suspension.

The dosage of the ulcer-treating agent can be suitably varied according to the degree of an ulcer to be treated, the condition of a patient, etc. Usually, it is about 10 to about 1,000 mg/day/kg of body weight. For example, in oral administration, the suitable dosage is about 100 to about 1,000 mg/day/kg of body weight, and in parenteral administration, the suitable dosage is about 10 to about 500 mg/day/kg of body weight.

The ulcer treating composition of this invention should include the active ingredient of formula (I) in amounts suitable for administration in the above-exemplified dosages, and its amount is, for example, about 0.1 to about 99% by weight.

The active ingredient of this invention has low toxicity. The acute toxicity of compounds Nos. 3, 14, and 17 shown in Table I was examined on SD male and female rats (four weeks old) both in oral administration and intravenous administration. In oral administration, LD$_{50}$ of these compounds was more than 5,000 mg/kg both on male and female rats, and in intravenous administration, LD$_{50}$ was more than 3,000 mg/kg. When 3,000 mg/kg of each of the compounds was orally administered for 21 consecutive days, no abnormal condition was observed in the subjects.

The following Examples illustrate the present invention in more detail.

EXAMPLE 1

N-propionyl-methylmethioninesulfonium chloride of the formula:

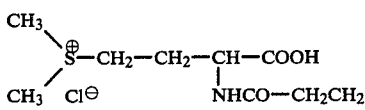

Pripionic anhydride (26 g) was added to a solution of 20 g of methylmethioninesulfonium chloride in 50 ml of acetic acid, and the mixture was stirred for one day at room temperature. Then, 1.5 liters of ethyl ether was added. The resulting jelly-like substance was separated, and chromatographed on a silica gel column with a mixture of acetone/methanol (4/1 to 3/1) as an eluent to afford 22.0 g (yield 86.0%) of N-propionyl-methylmethioninesulfonium chloride as colorless prisms having a melting point of 125° C. (decomp.).

Elemental analysis values for $C_9H_{18}O_3NSCl$

|  | C | H | N | S |
|---|---|---|---|---|
| Calculated (%): | 42.26 | 7.09 | 5.48 | 12.54 |
| Found (%): | 42.54 | 6.94 | 5.60 | 12.22 |

NMR (5–10% $D_2O$ solution, δ):
1.1 (3H, t, J=7 cps, $CH_3$),
2.2–2.7 (4H, m, S—$CH_2CH_2$, $COCH_2$),
3.0 (6H, s,

3.45 (2H, t, J=8 cps, S—$CH_2$),
4.65 (1H, q, J=7 cps, CH).

EXAMPLE 2

N-caprylyl-methylmethioninesulfonium chloride of the formula:

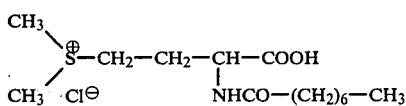

To a solution of 30 g of methylmethioninesulfonium chloride was added 100 ml of n-caprylic acid, and 81 g of n-caprylic anhydride was further added to emulsify the mixture. The resulting emulsion was stirred at 30° C. for one day. Then, 1 liter of ethyl ether was added. The resulting jelly-like substance was separated, and chromatographed on a silica gel column with a mixture of acetone/methanol (4/1) as an eluent to afford 30.9 g (yield 61.0%) of N-caprylylmethylmethioninesulfonium chloride as a pale yellow viscous oil.

Elemental analysis values for $C_{14}H_{28}O_3NSCl$

|  | C | H | N | S |
|---|---|---|---|---|
| Calculated (%): | 51.59 | 8.66 | 4.30 | 9.84 |
| Found (%): | 51.87 | 8.43 | 4.34 | 9,62 |

NMR (5–10% $D_2O$ solution, δ):
0.87 (3H, t, J=6 cps, $CH_3$),
1.0–1.9 (10H, m, $NHCOCH_2(CH_2)_5CH_3$),
2.0–2.6 (4H, m, S—$CH_2CH_2$, $\overline{COCH_2}$),
2.92 (6H, s,

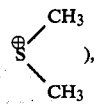

3.38 (2H, t, J=8 cps, S—$CH_2$),
4.38–4.68 (1H, m, CH).

EXAMPLE 3

N-benzoyl-methylmethioninesulfonium chloride of the formula:

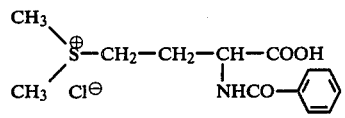

Benzoic anhydride (45.2 g) was added to a solution of 20 g of methylmethioninesulfonium chloride in 50 ml of acetic acid, and the mixture was stirred for 1 day at room temperature. Ethyl ether (200 ml) was added. The resulting jelly-like substance was separated and dissolved in a mixture of 15 ml of methanol and 15 ml of ethanol. Furthermore, 60 ml of ethyl ether was added, and the resulting jelly-like substance was separated. Upon standing, it solidified. Recrystallization from a mixture of methanol and acetone afforded 12.0 g (yield 40%) of N-benzoyl-methylmethioninesulfonium chloride as colorless needles having a melting point of 162° to 165° C. (decomp.).

Elemental analysis for $C_{15}H_{18}O_3NSCl$

|  | C | H | N | S |
|---|---|---|---|---|
| Calculated (%): | 51.40 | 5.97 | 4.61 | 10.55 |
| Found (%): | 51.17 | 6.06 | 4.72 | 10.23 |

NMR (5–10% $D_2O$ solution, δ):
2.1–2.65 (2H, m, S—$CH_2CH_2$),
2.95 (6H, s,

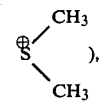

3.45 (2H, t, J=8 cps, S—$CH_2$),
4.55 (1H, q, J=8 cps, CH),
7.47–8.0 (5H, m, aromatic H).

By operating in the same way as in Examples 1 to 3, compounds of Examples 4 to 12 were prepared.

EXAMPLE 4

N-acetyl-methylmethioninesulfonium chloride of the formula:

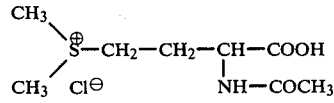

Yield: 74%
Form: pale yellow viscous oil
NMR (5–10% $D_2O$ solution, δ):
2.1 (3H, s, $COCH_3$), 3.0 (6H, s,

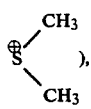

), 3.4 (2H, t, J=7 cps, S—CH₂),
4.56 (1H, q, J=7 cps, CH).

EXAMPLE 5

N-butyryl-methylmethioninesulfonium chloride of the formula:

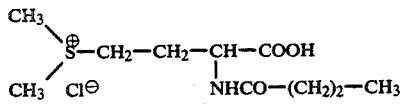

Yield: 51%
Form: pale yellow viscous oil
NMR (5-10% D₂O solution, δ):
0.9 (3H, t, J=7 cps, CH₃),
1.35-1.95 (2H, m, CH₂),
2.1-2.7 (4H, m, S—CH₂CH₂, COCH₂),
2.95 (6H, s,

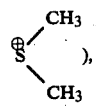

), 3.42 (2H, t, J=7 cps, S—CH₂).

EXAMPLE 6

N-isobutyryl-methylmethioninesulfonium chloride of the formula:

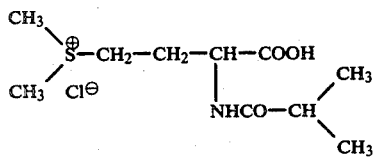

Yield: 39.5%
Form: colorless needles
Melting point: 142° C. (decomp.) (recrystallized from methanol/acetone/ether)
NMR (5-10% D₂O solution, δ):
1.1 (6H, d, J=6 cps,

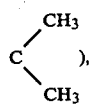

), 2.1-2.6 (3H, m, S—CH₂CH₂, COCH),
2.95 (6H, s,

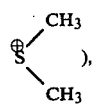

), 3.42 (2H, t, J=8 cps, S—CH₂), 4.55 (1H, q, J=8 cps, CH).

EXAMPLE 7

N-caproyl-methylmethioninesulfonium chloride of the formula:

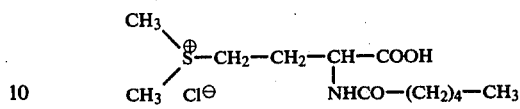

Yield: 51.2%
Form: pale yellow viscous oil
NMR (5-10% D₂O solution, δ):
0.86 (3H, t, J=6 cps, CH₃),
1.05-1.95 (6H, m, COCH₂(CH₂)₃),
1.95-2.65 (4H, m, S—CH₂CH₂, COCH₂),
2.96 (6H, s,

), 3.43 (2H, t, J=8 cps, S—CH₂),
4.6 (1H, q, J=8 cps, CH).

EXAMPLE 8

N-caprylyl-methylmethioninesulfonium chloride of the formula:

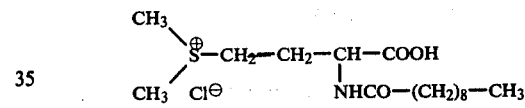

Yield: 25.4%
Form: pale yellow viscous oil
NMR (5-10% D₂O solution, δ):
0.85 (3H, t, J=5 cps, CH₃),
1.05-1.5 (14H, m, COCH₂(CH₂)₇CH₃),
2.1-2.65 (4H, m, S—CH₂CH₂, COCH₂),
2.95 (6H, s,

), 3.4 (2H, t, J=8 cps, S—CH₂),
4.4-4.7 (1H, m, CH).

EXAMPLE 9

N-lauroyl-methylmethioninesulfonium chloride of the formula:

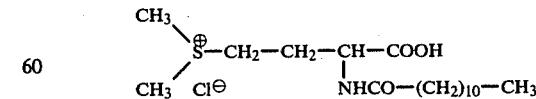

Yield: 20.9%
Form: pale yellow viscous oil
NMR (5-10% D₂O solution, δ):
0.85 (3H, t, J=5 cps, CH₃),
1.0-1.5 (18H, m, COCH₂(CH₂)₉CH₃),
2.1-2.6 (4H, m, S—CH₂CH₂, COCH₂), 2.95 (6H, s,

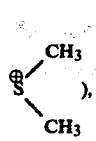
), 3.1–3.6 (2H, m, S—CH$_2$).

EXAMPLE 10

N-myristoyl-methylmethioninesulfonium chloride of the formula:

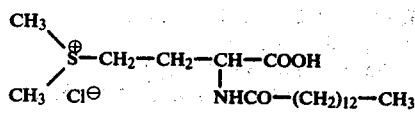

Yield: 40%
Form: pale yellow oil
NMR (5–10% D$_2$O solution, δ):
0.85 (3H, t, J=6 cps, CH$_3$),
1.0–1.5 (22H, m, COCH$_2$(CH$_2$)$_{11}$CH$_3$),
2.1–2.7 (4H, m, S—CH$_2$CH$_2$, COCH$_2$),
2.95 (6H, s,

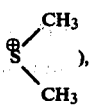
), 3.35 (2H, t, J=8 cps, S—CH$_2$).

Example 11

N-stearoyl-methylmethionesulfonium chloride of the formula

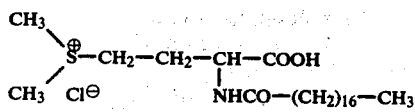

Yield: 16.3%
Form: colorless granular crystals
Melting point: 111° to 134° C. (decomp.) (recrystallized from methanol/ether)
NMR (5–10% CD$_3$OD solution, δ): 1.0–1.5 (30H, m, COCH$_2$(CH$_2$)$_{15}$CH$_3$), 3.0 [6H, s,

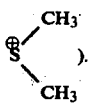
).

EXAMPLE 12

N-(3-carboxypropionyl)-methylmethioninesulfonium chloride of the formula:

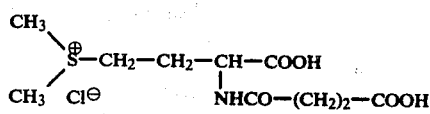

Yield: 80.7%
Form: colorless viscous oil
NMR (5–10% D$_2$O solution, δ):

2.1–2.7 (2H, m, S—CH$_2$CH$_2$),
2.63 (4H, s, COCH$_2$CH$_2$CO),
2.95 (6H, s,

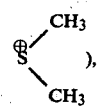
), 3.42 (2H, t, J=8 cps, S—CH$_2$),
4.7 (1H, q, J=8 cps, CH).

EXAMPLE 13

N-3,4,5-trimethoxybenzoyl-methylmethioninesulfonium chloride of the formula

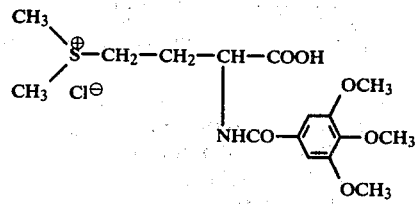

A solution of 30.1 g of 3,4,5-trimethoxybenzoyl chloride in 260 ml of chloroform was added dropwise at room temperature to a solution of 19.4 g of methionine in 260 ml of a 1N aqueous solution of sodium hydroxide, and the mixture was heated under reflux for 5 hours. After the reaction, the aqueous layer was separated, acidified with hydrochloride acid, and extracted with 300 ml of chloro form. The extract was concentrated to dryness, and the resulting residue was recrystallized from a mixture of acetone and n-hexane to afford 25.0 g (yield 56.0%) of N-3,4,5-trimethoxybenzoyl-methionine as colorless needles having a melting point of 177° to 178° C.

The resulting N-3,4,5-trimethoxybenzoyl-methionine (21.8 g) was suspended in 90 ml of water, and the suspension was heated to 60° C., and with stirring, 28.0 g of dimethyl sulfate was added dropwise over the course of 15 minutes. Furthermore, the mixture was stirred at 60° C. for 30 minutes. After the reaction, the reaction mixture containing the resulting N-3,4,5-trimethoxybenzoyl-methylmethioninesulfonium methosulfate was eluted through a column of Amberlite IRA-400 (a trademark for an OH-type ion exchange resin, a product of Room and Haas Co.) using water as a developing solvent. About 500 ml of the weakly alkaline eluate was adjusted to pH 2.0 with hydrochloric acid, and then the water was distilled off. Ethyl ether (200 ml) was added to the residue, and the mixture was filtered to afford a powder. Recrystallization of the powder from methanol/ether afforded 14.5 g (yield 58.0%) of N-3,4,5-trimethoxybenzoyl-methylmethioninesulfonium chloride as a colorless powder having a melting point of 67° to 70° C.

Elemental analysis values for C$_{16}$H$_{24}$O$_6$NSCl:

|  | C | H | N | S |
|---|---|---|---|---|
| Calculated (%): | 48.79 | 6.14 | 3.56 | 8.14 |
| Found (%): | 48.92 | 6.12 | 3.63 | 8.06 |

NMR (5–10% D$_2$O solution, δ):
2.2–2.87 (2H, m, S—CH$_2$CH$_2$),
3.03 (6H, s, S⊕ (CH$_3$)$_2$), 3.50 (2H, t, J=8 cps, S—CH$_2$),
3.85 (3H, s, 4—OCH$_3$),
3.90 (6H, s, 3,5—(OCH$_3$)$_2$),
7.09 (2H, s, aromatic H).

By operating in the same way as in Example 13, compounds of Examples 14 to 21 were prepared.

EXAMPLE 14

N-4-methoxybenzoyl-methylmethioninesulfonium chloride of the formula:

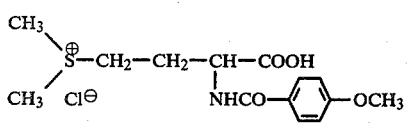

Yield: 36%
Form: 141.5°–144° C. (decomp.) (recrystallized from methanol/acetone)
NMR (5–10% D$_2$O solution, δ):
2.25–2.9 (2H, m, S—CH$_2$CH$_2$),
3.0 (6H, s, S$^⊕$ (CH$_2$)$_2$),
3.55 (2H, t, J=8 cps, S—CH$_2$),
3.92 (3H, s, OCH$_3$),
4.8 (1H, m, CH),
7.11 (2H, d, J=9 cps, 3,5—(H)$_2$),
7.89 (2H, d, J=9 cps, 2,6—(H)$_2$).

EXAMPLE 15

N-2-methoxybenzoyl-methylmethioninesulfonium chloride of the formula:

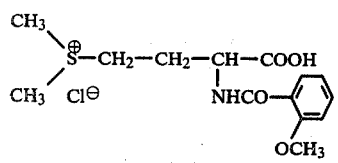

Yield: 35%
Form: colorless needles
Melting point: 141° to 143° C. (decomp.) (recrystallized from methanol/acetone)
NMR (5–10% D$_2$O solution, δ):
2.35–2.84 (2H, m, S—CH$_2$CH$_2$),
3.0 (6H, s, S$^⊕$ (CH$_3$)$_2$),
3.53 (2H, t, J=8 cps, S—CH$_2$),
4.03 (3H, s, OCH$_3$),
7.0–8.08 (4H, m, aromatic H).

EXAMPLE 16

N-2-methoxy-5-sulfamoylbenzoyl-methylmethioninesulfonium chloride of the formula:

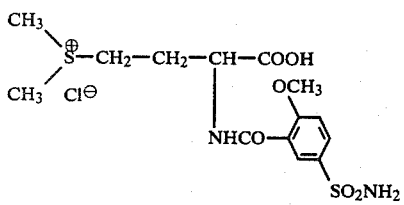

Yield: 83%
Form: colorless needles
Melting point: 160° C. (decomp.) (recrystallized from methanol/acetone)

NMR (5–10% D$_2$O solution, δ):
2.28–2.84 (2H, m, S—CH$_2$CH$_2$),
3.0 (6H, s, S$^⊕$ (CH$_3$)$_2$),
3.58 (2H, t, J=8 cps, S—CH$_2$),
4.08 (3H, s, OCH$_3$),
7.26 (1H, d, J=9 cps, 3—H),
8.02 (1H, d, J=3 cps, d, J=9 cps, 4—H),
8.25 (1H, d, J=3 cps, 6—H).

EXAMPLE 17

N-4-methylbenzoyl-methylmethioninesulfonium chloride of the formula:

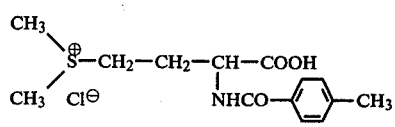

Yield: 76%
Form: colorless prisms
Melting point: 166° C. (decomp.) (recrystallized from methanol/acetone)
NMR (5–10% D$_2$O solution, δ):
2.4–2.8 (2H, m, S—CH$_2$CH$_2$),
2.45 (3H, s, 4—CH$_3$),
3.05 (6H, s, S$^⊕$ (CH$_3$)$_2$),
3.55 (2H, t, J=8 cps, S—CH$_2$),
7.40 (2H, d, J=9 cps, 3,5—(H)$_2$),
7.85 (2H, d, J=9 cps, 2,6—(H)$_2$).

EXAMPLE 18

N-4-dimethylaminobenzoyl-methylmethioninesulfonium chloride of the formula:

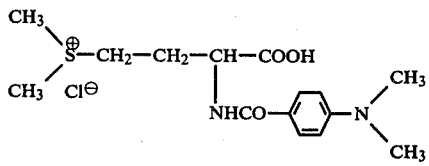

Yield: 38%
Form: colorless needles
Melting point: 160° to 162° C. (decomp.) (recrystallized from methanol/acetone)
NMR (5–10% D$_2$O solution, δ):
2.33–2.78 (2H, m, S—CH$_2$CH$_2$),
3.0 (6H, s, S$^⊕$ (CH$_3$)$_2$),
3.24 (6H, s, N(CH$_3$)$_2$),
3.5 (2H, t, J=8 cps, S—CH$_2$),
7.45 (2H, d, J=9 cps, 3,5—(H)$_2$),
7.98 (2H, d, J=9 cps, 2,6—(H)$_3$).

EXAMPLE 19

N-nicotinoyl-methylmethioninesulfonium chloride of the formula:

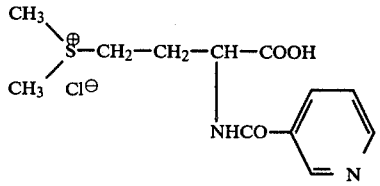

Yield: 36%

Form: colorless powder
Melting point: 82° C. (decomp.) (recrystallized from methanol/acetone/ether
NMR (5-10% D₂O solution, δ):
2.32-2.85 (2H, m, S—CH₂CH₂),
3.0 (6H, s, S⊕ (CH₃)₂),
3.55 (2H, d, J=8 cps, S—CH₂),
8.05 (1H, q, J=8 cps, H_B),
8.7-9.25 (3H, m, H_A, H_C, H_D).

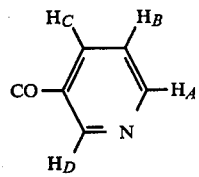

EXAMPLE 20

N-phenylacetyl-methylmethioninesulfonium bisulfate of the formula:

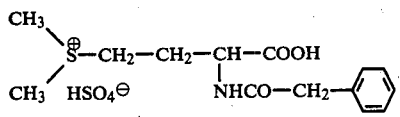

Yield: 41%
Form: colorless prisms
Melting point: 135° C. (decomp.) (recrystallized from methanol/acetone)
NMR (5-10% D₂O solution, δ):
2.15-2.6 (2H, m, CH₂),
2.85 (6H, s, S⊕ (CH₃)₂),
3.28 (2H, t, J=8 cps, S—CH₂),
3.7 (2H, s, COCH₂),
4.58 (1H, q, J=8 cps, CH),
7.45 (5H, s, aromatic H).

EXAMPLE 21

N-cinnamoyl-methylmethioninesulfonium chloride of the formula:

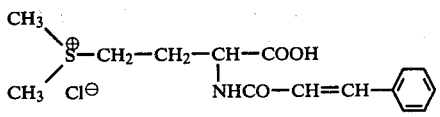

Yield: 37%
Form: colorless needles
Melting point: 129°-132° C. (decomp.) (recrystallized from methanol/acetone/ether)
NMR (5-10% D₂O solution, δ):
2.35-2.86 (2H, m, S—CH₂CH₂),
3.14 (6H, s, S⊕ (CH₃)₂),
3.63 (2H, t, J=8 cps, S—CH₂),
4.7-5.03 (1H, m, CH)
6.85 (1H, d, J=8 cps, COCH=),
7.37-7.93 (6H, m,

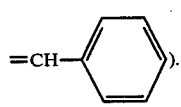).

EXAMPLE 22

Methylmethioninesulfonium chloride ethyl ester hydrochloride of the formula

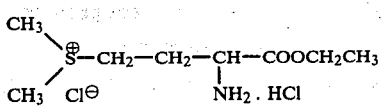

Methylmethioninesulfonium chloride (40 g) was suspended in 400 ml of ethanol, and while the suspension was being cooled to 0° to −6° C., 48 g of thionyl chloride was added dropwise. After the addition, the mixture was heated to 50° C., and stirred for 20 hours. After the reaction, 500 ml of ethyl ether and 200 ml of acetone were added to the reaction mixture. The resulting jelly-like substance was separated and recrystallized from a mixture of methanol, ethanol and acetone to afford 30.5 g (yield 57.6%) of methylmethioninesulfonium chloride ethyl ester hydrochloride having a melting point of 136° to 138° C. (decomp.).

Elemental analysis values for $C_8H_{19}O_2NSCl_2$:

|  | C | H | N | S |
|---|---|---|---|---|
| Calculated (%): | 36.51 | 6.89 | 5.32 | 12.13 |
| Found (%): | 36.78 | 7.09 | 5.43 | 12.23 |

NMR (5-10% D₂O solution, δ):
1.34 (3H, t, J=7 cps, CH₃),
2.3-2.8 (2H, m, S—CH₂CH₂),
3.0 (6H, s, S⊕ (CH₃)₂),
3.4-3.7 (2H, m, S—CH₂),
4.38 (1H, t, J=6 cps, CH),
4.4 (2H, q, J=7 cps, COOCH₂).

By operating in the same way as in Example 22, compounds of Examples 23 to 31 were prepared.

EXAMPLE 23

Methylmethioninesulfonium chloride methyl ester hydrochloride of the formula:

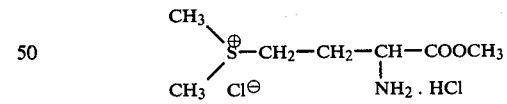

Yield: 67.4%
Form: colorless needles
Melting point: 135° to 137° C. (recrystallized from ethanol/methanol/ether)
NMR (5-10% D₂O solution, δ):
2.15-2.79 (2H, m, S—CH₂CH₂),
3.0 (6H, s, S⊕ (CH₃)₂),
3.46-3.71 (2H, m, S—CH₂),
3.90 (3H, s, COOCH₃),
4.38 (1H, t, J=6 cps, CH).

EXAMPLE 24

Methylmethioninesulfonium chloride butyl ester hydrochloride of the formula:

$$\begin{array}{c}CH_3\\ \diagdown\overset{\oplus}{S}-CH_2-CH_2-\underset{\underset{NH_2\cdot HCl}{|}}{CH}-COO-(CH_2)_3-CH_3\\ CH_3\diagup\ Cl^{\ominus}\end{array}$$

Yield: 37.4%
Form: colorless viscous oil
NMR (5–10% D$_2$O solution, δ):
0.93 (3H, t, J=6 cps, CH$_3$),
1.16–2.04 (4H, m, COOCH$_2$(CH$_2$)$_2$CH$_3$),
2.15–2.84 (2H, m, S—CH$_2$CH$_2$),
3.03 (6H, s, S$^\oplus$ (CH$_3$)$_2$),
3.48–3.82 (2H, m, S—CH$_2$),
4.23–4.52 (3H, m, CH, COOCH$_2$).

EXAMPLE 25

N-acetyl-methylmethioninesulfonium chloride methyl ester of the formula:

$$\begin{array}{c}CH_3\\ \diagdown\overset{\oplus}{S}-CH_2-CH_2-\underset{\underset{NHCOCH_3}{|}}{CH}-COOCH_3\\ CH_3\diagup\ Cl^{\ominus}\end{array}$$

Yield: 36.8%
Form: colorless prisms (recrystallized from methanol/acetone; m.p. 123° C., decomp.)
NMR (5–10% D$_2$O solution, δ):
2.10 (3H, s, COCH$_3$),
2.2–2.65 (2H, m, S—CH$_2$CH$_2$),
2.95 (6H, s, S$^\oplus$ (CH$_3$)$_2$),
3.42 (2H, t, J=8 cps, S—CH$_2$),
3.85 (3H, s, COOCH$_3$).

EXAMPLE 26

N-acetyl-methylmethioninesulfonium chloride, ethyl ester of the formula:

$$\begin{array}{c}CH_3\\ \diagdown\overset{\oplus}{S}-CH_2-CH_2-\underset{\underset{NHCOCH_3}{|}}{CH}-COOCH_2CH_3\\ CH_3\diagup\ Cl^{\ominus}\end{array}$$

Yield: 49.0%
Form: pale yellow viscous oil
NMR (5–10% D$_2$O solution, δ):
1.30 (3H, t, J=7 cps, CH$_3$),
2.08 (3H, s, COCH$_3$),
2.15–2.6 (2H, m, S—CH$_2$CH$_2$),
2.92 (6H, s, S$^\oplus$ (CH$_3$)$_2$),
3.40 (2H, t, J=7 cps, S—CH$_2$),
4.27 (2H, q, J=7 cps, COOCH$_2$).

EXAMPLE 27

N-acetyl-methylmethioninesulfonium chloride, propyl ester of the formula:

$$\begin{array}{c}CH_3\\ \diagdown\overset{\oplus}{S}-CH_2-CH_2-\underset{\underset{NHCOCH_3}{|}}{CH}-COOCH_2CH_2CH_3\\ CH_3\diagup\ Cl^{\ominus}\end{array}$$

Yield: 48.0%
Form: pale yellow viscous oil
NMR (5–10% D$_2$O solution, δ):
0.93 (3H, t, J=7 cps, CH$_3$),
1.40–1.95 (2H, m, COOCH$_2$CH$_2$CH$_3$),
2.10 (3H, s, COCH$_3$),
2.2–2.65 (2H, m, S—CH$_2$CH$_2$),
2.97 (6H, s, S$^\oplus$ (CH$_3$)$_2$),
3.42 (2H, t, J=8 cps, s—CH$_2$),
4.14 (2H, t, J=7 cps, COOCH$_2$).

EXAMPLE 28

N-acetyl-methylmethioninesulfonium chloride, butyl ester of the formula:

$$\begin{array}{c}CH_3\\ \diagdown\overset{\oplus}{S}-CH_2-CH_2-\underset{\underset{NHCOCH_3}{|}}{CH}-COO-(CH_2)_3-CH_3\\ CH_3\diagup\ Cl^{\ominus}\end{array}$$

Yield: 59.0%
Form: pale yellow viscous oil
NMR (5–10% D$_2$O solution, δ):
0.90 (3H, t, J=7 cps, CH$_3$),
1.05–1.85 (4H, m, COOCH$_2$(CH$_2$)$_2$CH$_3$),
2.07 (3H, s, COCH$_3$),
2.10–2.65 (2H, m, S—CH$_2$CH$_2$),
2.93 (6H, m, S$^\oplus$ (CH$_3$)$_2$),
3.45 (2H, t, J=8 cps, S—CH$_2$),
4.18 (2H, t, J=7 cps, COOCH$_2$).

EXAMPLE 29

N-caprylyl-methylmethioninesulfonium chloride, methyl ester of the formula:

$$\begin{array}{c}CH_3\\ \diagdown\overset{\oplus}{S}-CH_2-CH_2-\underset{\underset{NHCO-(CH_2)_6-CH_3}{|}}{CH}-COOCH_3\\ CH_3\diagup\ Cl^{\ominus}\end{array}$$

Yield: 44.1%
Form: pale yellow viscous oil
NMR (5–10% D$_2$O solution, δ):
0.87 (3H, t, J=6 cps, CH$_3$),
1.0–1.6 (10H, m, COCH$_2$(CH$_2$)$_5$CH$_3$),
2.08–2.67 (4H, m, S—CH$_2$CH$_2$.COCH$_2$),
3.01 (6H, s, S$^\oplus$ (CH$_3$)$_2$),
3.48 (2H, t, J=8 cps, S—CH$_2$),
3.80 (3H, s, COOCH$_3$).

EXAMPLE 30

N-caprylyl-methylmethioninesulfonium chloride, ethyl ester of the formula:

$$\begin{array}{c}CH_3\\ \diagdown\overset{\oplus}{S}-CH_2-CH_2-\underset{\underset{NHCO-(CH_2)_6-CH_3}{|}}{CH}-COOCH_2CH_3\\ CH_3\diagup\ Cl^{\ominus}\end{array}$$

Yield: 52.5%
Form: pale yellow viscous oil
NMR (5–10% D$_2$O solution, δ):
0.87 (3H, t, J=6 cps, CH$_3$),
1.02–1.5 (13H, m, COCH$_2$(CH$_2$)$_5$CH$_3$.CH$_2$CH$_3$),
2.0–2.64 (4H, m, S—CH$_2$CH$_2$.COCH$_2$)
2.98 (6H, s, S$^\oplus$ (CH$_3$)$_2$),
3.48 (2H, t, J=8 cps, S—CH$_2$),
4.23 (2H, q, J=6 cps, COOCH$_2$).

EXAMPLE 31

N-caprylyl-methylmethioninesulfonium chloride, propyl ester of the formula:

$$\begin{array}{c} CH_3 \\ \phantom{CH_3}\diagdown\!\!\!\overset{\oplus}{S}\!\!-\!CH_2\!-\!CH_2\!-\!\underset{|}{CH}\!-\!COOCH_2CH_2CH_3 \\ CH_3 \phantom{\diagdown\!\!\!\overset{\oplus}{S}}\ Cl^{\ominus} \phantom{\!-\!CH_2\!-\!CH_2\!-\!CH\!-} NHCO\!-\!(CH_2)_6\!-\!CH_3 \end{array}$$

Yield: 46.0%
Form: light yellow viscous oil
NMR (5–10% $D_2O$ solution, δ):
0.62–1.1 (6H, m, 2CH$_3$),
1.1–2.0 (10H, m, COCH$_2$(C$\underline{H_2}$)$_5$CH$_3$),
2.0–2.62 (4H, m, S—CH$_2$C$\underline{H_2}$.COCH$_2$),
2.96 (6H, s, S$^\oplus$ (CH$_3$)$_2$),
3.46 (2H, t, J=8 cps, S—CH$_2$).

EXAMPLE 32

Methylmethionylethylamide sulfonium chloride of the formula:

$$\begin{array}{c} CH_3 \\ \phantom{CH_3}\diagdown\!\!\!\overset{\oplus}{S}\!\!-\!CH_2\!-\!CH_2\!-\!\underset{|}{CH}\!-\!CONH\!-\!CH_2CH_3 \\ CH_3 \phantom{\diagdown\!\!\!\overset{\oplus}{S}}\ Cl^{\ominus} \phantom{\!-\!CH_2\!-\!CH_2\!-\!CH\!-} NH_2 \end{array}$$

Methionine methyl ester (5 g) was dissolved in 20 ml of ethylamine, and reacted for several days at 4° to 6° C. When the excess of ethylamine was distilled off from the reaction mixture, 5.2 g (yield 96.3%) of methionyl ethylamide as a pale yellow viscous oil was obtained. The product was dissolved in 20 ml of water, and heated to 60° C. Dimethyl sulfate (5.58 g) was added dropwise, and the reaction was performed at the same temperature for 45 minutes with stirring. Water (20 ml) was added to the resulting reaction mixture containing methylmethionylethylamide sulfonium methosulfate, and the mixture was passed through a column of Amberlite IRA 400 (a trademark for an OH-type ion exchange resin, a product of Rhom and Haas Co.) using water as an eluent. The resulting eluate (300 ml) was adjusted to pH 3.0 with hydrochloric acid, and water was distilled off. The residue was chromatographed on a silica gel column with a mixture of acetone and methanol (4/1) as an eluent to afford 1.8 g (yield 26.9%) of methylmethionineethylamide sulfonium chloride as a pale yellow viscous oil.

Elemental analysis for C$_8$H$_{19}$ON$_2$SCl:

|  | C | H | N | S |
|---|---|---|---|---|
| Calculated (%): | 42.37 | 7.12 | 12.35 | 14.14 |
| Found (%): | 42.77 | 6.77 | 12.42 | 13.94 |

NMR (5–10% $D_2O$ solution, δ):
1.12 (3H, t, J=7 cps, CH$_3$),
2.31–2.58 (4H, m, S—C$\underline{H_2}$C$\underline{H_2}$.NHCH$_2$CH$_3$),
2.96 (6H, s, S$^\oplus$ (SCH$_3$)$_2$),
3.08–3.55 (2H, m, S—CH$_2$C$\underline{H_2}$),
4.11 (1H, t, J=7 cps, CH).

EXAMPLE 33

Methylmethionylbutylamidesulfonium chloride of the formula:

$$\begin{array}{c} CH_3 \\ \phantom{CH_3}\diagdown\!\!\!\overset{\oplus}{S}\!\!-\!CH_2\!-\!CH_2\!-\!\underset{|}{CH}\!-\!CONH\!-\!(CH_2)_3\!-\!CH_3 \\ CH_3 \phantom{\diagdown\!\!\!\overset{\oplus}{S}}\ Cl^{\ominus} \phantom{\!-\!CH_2\!-\!CH_2\!-\!CH\!-} NH_2 \end{array}$$

In the same way as in Example 32, the reaction was performed for 6 days at room temperature using n-butylamine instead of the ethylamine. The same treatment of the reaction mixture as in Example 32 afforded methylmethionylbutylamide sulfonium chloride as a pale yellow viscous oil in a yield of 33.4%.

Elemental analysis for C$_{10}$H$_{23}$ON$_2$SCl:

|  | C | H | N | S |
|---|---|---|---|---|
| Calculated (%): | 47.14 | 9.10 | 10.99 | 12.58 |
| Found (%): | 47.34 | 9.25 | 11.15 | 12.78 |

NMR (5–10% $D_2O$ solution, δ):
0.61–1.07 (3H, m, CH$_3$),
1.07–1.74 (6H, m, NH—(C$\underline{H_2}$)$_3$CH$_3$),
2.11–2.54 (2H, m, S—C$\underline{H_2}$CH$_2$),
3.04–3.41 (2H, m, S—CH$_2$),
2.93 (6H, s, S$^\oplus$ (CH$_3$)$_2$),
3.92–4.19 (1H, m, CH).

EXAMPLE 34

N-acetylmethylmethioninamide sulfonium chloride of the formula:

$$\begin{array}{c} CH_3 \\ \phantom{CH_3}\diagdown\!\!\!\overset{\oplus}{S}\!\!-\!CH_2\!-\!CH_2\!-\!\underset{|}{CH}\!-\!CONH_2 \\ CH_3 \phantom{\diagdown\!\!\!\overset{\oplus}{S}}\ Cl^{\ominus} \phantom{\!-\!CH_2\!-\!CH_2\!-\!CH\!-} NHCOCH_3 \end{array}$$

A solution of 24 g of ammonia gas in 100 ml of methanol was added to a solution of 10 g of N-acetylmethylmethioninesulfonium chloride, methyl ester in 30 ml of methanol, and they were reacted at room temperature for 2 days. After the reaction, the solvent was distilled off. The residue was chromatographed on a silica gel column with a mixture of methanol and acetone (8:1 to 4:1) as an eluent to afford 7.6 g (yield 80.7%) of N-acetyl-methylmethioninamide sulfonium chloride as a pale yellow viscous oil.

NMR (5–10% $D_2O$ solution, δ):
2.10 (3H s, COCH$_3$),
2.1–2.6 (2H, m, S—C$\underline{H_2}$CH$_2$),
2.97 (6H, s, S$^\oplus$ (CH$_3$)$_2$),
3.43 (2H, t, J=8 cps, S—CH$_2$),
4.55 (1H, t, J=6 cps, CH).

EXAMPLE 35

N-caprylyl-methylmethionineamide sulfonium chloride of the formula:

$$\begin{array}{c} CH_3 \\ \phantom{CH_3}\diagdown\!\!\!\overset{\oplus}{S}\!\!-\!CH_2\!-\!CH_2\!-\!\underset{|}{CH}\!-\!CONH_2 \\ CH_3 \phantom{\diagdown\!\!\!\overset{\oplus}{S}}\ Cl^{\ominus} \phantom{\!-\!CH_2\!-\!CH_2\!-\!CH\!-} NHCO\!-\!(CH_2)_6\!-\!CH_3 \end{array}$$

A solution of 36 g of ammonia gas in 150 ml of methanol was added to a solution of 15 g of N-caprylyl-methylmethioninesulfonium chloride methyl ester in 50 ml of methanol, and they are reacted for 2 days at room temperature. After the reaction, the solvent was distilled off, and the residue was chromatographed on a silica gel column with a mixture of acetone/methanol (7/1 to 4/1) as an eluent. The solvent was distilled off from the eluate, and the resulting powder was recrystallized from ethanol/acetone to afford 8 g (yield 55.8%) of N-caprylyl-methylmethioninamide sulfonium chloride as colorless needles having a melting point of 97° C. (decomp.).

Elemental analysis for $C_{14}H_{20}O_2N_2Cl$:

Elemental analysis for $C_{40}H_{70}O_{19}N_5S_5Cl_3Al_3$:

|  | C | H | N | S |
|---|---|---|---|---|
| Calculated (%): | 35.52 | 5.89 | 5.18 | 11.85 |
| Found (%): | 35.11 | 6.22 | 5.22 | 11.83 |

EXAMPLE 37–42

By operating in the same way as in Example 36, compounds shown in the following table were prepared.

$$Z_5Al_3(OH)_4 \left[ Z = \begin{array}{c} CH_3 \\ \diagdown \overset{\oplus}{S} - CH_2 - CH_2 - CH - COO \\ \diagup Cl^{\ominus} \qquad \qquad | \\ CH_3 \qquad \qquad NH - CO - Q \end{array} \right]$$

| Example | Q | Yield (%) | Form | Melting point (°C.) | Molecular formula |
|---|---|---|---|---|---|
| 37 | $CH_2CH_3$ | 68.0 | Colorless powder |  | $C_{45}H_{89}O_{19}N_5S_5Cl_5Al_3$ |
| 38 | $CH_2CH_2CH_3$ | 42.9 | Colorless powder |  | $C_{50}H_{99}O_{19}N_5S_5Cl_5Al_3$ |
| 39 | $CH(CH_3)_2$ | 57.8 | Colorless powder |  | " |
| 40 | $(CH_2)_4CH_3$ | 64.8 | Colorless powder |  | $C_{60}H_{119}O_{19}N_5S_5Cl_5Al_3$ |
| 41 | $(CH_2)_8CH_3$ | 73.5 | Colorless powder |  | $C_{70}H_{139}O_{19}N_5S_5Cl_5Al_3$ |
| 42 | $C_6H_5$ | 78.9 | Colorless powder | 105 (decomp.) | $C_{65}H_{89}O_{19}N_5S_5Cl_5Al_3$ |

|  | C | H | N | S |
|---|---|---|---|---|
| Calculated (%): | 51.75 | 9.00 | 8.62 | 9.87 |
| Found (%): | 51.19 | 8.82 | 8.59 | 9.83 |

NMR (5–10% $D_2O$ solution, $\delta$):
0.85 (3H, t, J=6 cps, $CH_3$),
1.03–1.82 (10H, m, $COCH_2(\underline{CH_2})_5CH_3$),
2.2–2.7 (4H, m, S—$CH_2\underline{CH_2}$, $\overline{COCH_2}$),
2.97 (6H, s, $S^\oplus$ $(CH_3)_2$),
3.45 (2H, t, J=8 cps, S—$CH_2$).

EXAMPLE 36

Aluminum N-acetyl-methylmethionine sulfonium chloride of the formula:

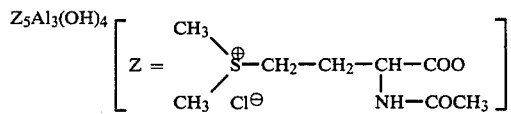

A suspension of 9.7 g of aluminum isopropoxide in 14 ml of isopropanol was added to a solution of 23 g of N-acetyl-methylmethioninesulfonium chloride in 96 ml of water with stirring at 60° C. The mixture was stirred further for 1.5 hours, and isopropanol was distilled off. Water (100 ml) was added, and the resulting emulsion was filtered using cerite. The filtrate was concentrated to produce 24 g of a jelly-like substance. It was dissolved in 5 ml of methanol, and 50 ml of acetone and 50 ml of ethyl ether were added. The solvent was removed by decantation, and the residue was mixed with 50 ml of acetone and 50 ml of ethyl ether and purified to afford 20.0 g (yield 77.8%) of aluminum N-acetyl-methylmethioninesulfonium chloride as a colorless powder having a melting point of 138° C. (decomp.).

Some typical examples of the compound of this invention were pharmacologically tested, and the results are shown below.

Test No. I: Inhibitory activity on aspirin-induced ulcers.

Rats, 10 in each group, were divided into a nonadministered group (control) and administered groups. Each of the test compounds was administered orally in the dosages shown in Table A below, and one hour later, aspirin was orally administered in a dose of 70 mg/kg. One hour after the administration of aspirin, the rats were killed. The diameters of ulcers generated in the stomach were measured in each rat, and the total of the diameters of all the ulcers was defined as an ulcer index. Aspirin was administered to the control group in the same way as above except that no test compounds was administered. The results are shown in Table A. In the following tables, the numbers of the test compounds correspond to those of the compounds shown in Table I hereinabove.

Table A

| Test compound | Dosage (mg/kg, p.o.) | Ulcer index mm (mean ± S.E) | Percent inhibition (%) |
|---|---|---|---|
| Control | — | 90 ± 7.4 | — |
| No. 3 | 100 | 66 ± 11 | 27 |
| No. 3 | 300 | 35 ± 8.7 | 61 |
| No. 8 | 100 | 18.9 ± 4 | 79 |
| No. 14 | 100 | 104 ± 9 | — |
| No. 14 | 300 | 12 ± 3 | 87 |
| MMSC (compari- | 300 | 51 ± 13 | 43 |

Table A-continued

| Test compound | Dosage (mg/kg, p.o.) | Ulcer index mm (mean ± S.E) | Percent inhibition (%) |
|---|---|---|---|
| son) | | | |

Note

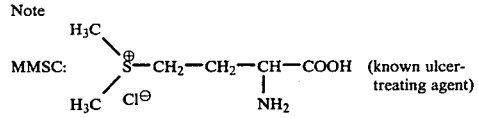

MMSC: (known ulcer-treating agent)

Test No. II: Inhibitory activity on acetic acid-induced ulcers.

Rats, 10 in each group, were divided into a non-administered group (control), and administered groups.

0.05 ml of a 10% aqueous solution of acetic acid was injected into the subserous membrane of the glandular part of the rats to generate ulcers. On the 8th day after generation, the rats were killed, and the areas of ulcers generated in the stomach were measured, and made an ulcer index. Each of the test compounds was administered orally in the dosages shown in Table B twice a day for 7 days beginning on the day next to the day of ulcer generation.

The results are shown in Table B.

Table B

| Test compound | Dosage (mg/kg, p.o.) | Ulcer index mm (mean ± S.E) | Percent inhibition (%) |
|---|---|---|---|
| Control | — | 10.5 ± 1.8 | — |
| No. 3 | 100 | 5.8 ± 1.2 | 44.8 |
| No. 3 | 300 | 3.8 ± 1.8 | 63.8 |
| No. 14 | 100 | 10.5 ± 0.5 | — |
| No. 14 | 300 | 6.5 ± 1.8 | 38.0 |
| No. 17 | 100 | 9.0 ± 1.8 | 14.3 |
| No. 17 | 300 | 4.0 ± 0.9 | 61.9 |
| No. 25 | 100 | 7.1 ± 1.2 | 32.9 |
| No. 25 | 300 | 3.7 ± 0.9 | 65.1 |
| MMSC (comparison) | 100 | 9.2 ± 1.0 | 12.2 |
| MMSC (comparison) | 300 | 8.1 ± 1.6 | 22.9 |

Test No. III: Inhibitory activity on compound 48/80-induced ulcers

Rats, 10 in each group, were divided into a non-administered group (control) and administered groups.

Each of the test compounds was orally administered to the rats in the dosages shown in Table C. Thirty minutes later, 2 mg/kg of compound 48/80 was injected subcutaneously to the rats. The rats were killed 3 hours later and an ulcer index was determined on the ulcers generated on the mucous membrane of the stomach in the same way as in Test No. I. The results are shown in Table C.

Table C

| Test compound | Dosage (mg/kg, p.o.) | Ulcer index mm (mean ± S.E) | Percent inhibition (%) |
|---|---|---|---|
| Control | — | 19 ± 1.8 | — |
| No. 3 | 100 | 12 ± 1.7 | 37 |
| No. 3 | 300 | 5 ± 0.9 | 71 |
| No. 14 | 100 | 13 ± 2.0 | 32 |
| No. 14 | 300 | 5 ± 0.8 | 74 |
| MMSC (comparison) | 300 | 6 ± 0.5 | 67 |

Test No. IV: Inhibitory activity on stress-induced ulcers

Rats, 10 in each group, were divided into a non-administered group (control), and administered groups.

The rats were fasted for 15 hours, and each animal was immobilized in each compartment of the stress cage. The cages were then immersed in a water bath kept on 23° C. for 7 hours. Then, the rats were killed, and the lengths of ulcers generated in the stomach were measured and defined as an ulcer index.

The test compounds were orally administered in the dosages shown in Table D at the same time as the application of stress.

The results are shown in Table D.

Table D

| Test compound | Dosage (mg/kg, p.o.) | Ulcer index mm (mean ± S.E) | Percent inhibition (%) |
|---|---|---|---|
| Control | — | 16.7 ± 2.9 | — |
| No. 3 | 100 | 70.4 ± 5.2 | — |
| No. 3 | 300 | 9.2 ± 1.6 | 45 |
| No. 14 | 100 | 9.4 ± 1.1 | 44 |
| No. 14 | 300 | 8.7 ± 1.5 | 48 |
| No. 36 | 100 | 14.7 ± 0.1 | 12 |
| No. 36 | 300 | 8.8 ± 0.5 | 47 |
| MMSC (comparison) | 200 | 15.0 ± 2.0 | 10 |
| MMSC (comparison) | 400 | 12.2 ± 1.9 | 27 |

Test No. V: Activity on the regional mucosal blood flow

Dogs were used as experimental animals. A plate-type electrode was set in the submucosal layer at the center of the anterior wall of the stomach of the dogs while the dogs were incised under anaesthesia. By the thermocouple method, the blood flow in the mucous membrane of the stomach was measured. Each of the test compounds was intravenously administered in the dosages shown in Table E one hour after the setting of the electrode.

The results are shown in Table E.

Table E

| Test compound | Dosage (mg/kg, p.o.) | Increase (%) in the blood flow of the mucous membrane of the stomach |
|---|---|---|
| No. 3 | 30 | 54 |
| No. 3 | 100 | 182 |
| No. 14 | 30 | 29 |
| No. 14 | 100 | 173 |
| No. 17 | 30 | 19 |
| No. 17 | 100 | 152 |
| MMSC (comparison) | 30 | 10 |
| MMSC (comparison) | 100 | 65 |

Test No. VI: Activity on the blood flow in the left gastric artery

Dogs treated with heparin were incised under anaesthesia, and a probe of an electromagnetic flow meter was set in the gastric artery.

Each of the test compounds was injected intramuscularly into the left gastric artery one hour after the mount of the probe.

The results are shown in Table F.

Table F

| Compound | Dosage (mg/kg, i.a.) | Amount increased of the blood flow in the left gastric artery (ml/min.) |
|---|---|---|
| No. 1 | 10 | 14.0 |

Table F-continued

| Compound | Dosage (mg/kg, i.a.) | Amount increased of the blood flow in the left gastric artery (ml/min.) |
|---|---|---|
| No. 2 | 10 | 23.6 |
| No. 4 | 10 | 11.2 |
| No. 5 | 10 | 10.8 |
| No. 7 | 10 | 9.5 |
| MMSC (comparison) | 10 | 6.2 |

Test No. VII: Activity on acid secretion upon stimulation by gastrin

Under anaesthesia, the inside of the stomach of a dog was irrigated with a physiological saline solution, and the irrigated liquid flowing from a canule inserted in the pylorus was collected every 10 minutes. The total acidity of the irrigated liquids was measured by using a 0.1 N aqueous solution of sodium hydroxide. When the total acidity of the irrigated liquid became constant, gastrin was continuously injected into the vein in an amount of 1 g/kg/hr. Ninety minutes after the injection of gastrin, each of the test compounds was intravenously injected. The results were evaluated by the percentage of the total acidity after administration of the test compounds as against the total acidity at 90 minutes after the injection of gastrin.

Figure 2:
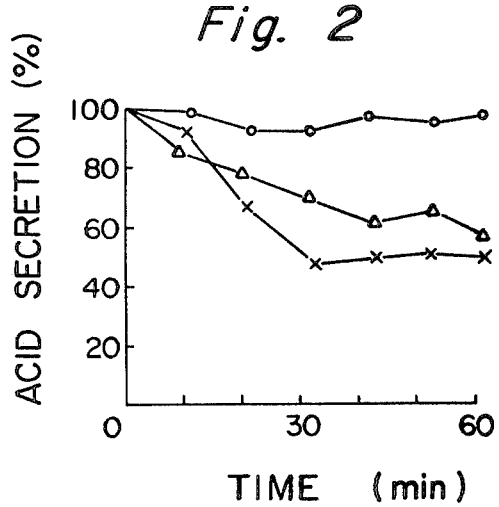

The results obtained with compounds Nos. 3 (FIG. 1), No. 7 (FIG. 2), No. 13 (FIG. 3), and No. 14 (FIG. 14) are shown in the accompanying drawings. In the drawings, —0 —0 — represents the results with a control group (not administered with the test compounds); —Δ—Δ— ,the results with a group administered with 30 mg/kg of the test compound; and —X —X —, the results with a group administered with 100 mg/kg of the test compound.

It can be seen from FIGS. 1 to 4 that the compounds of this invention have an action of inhibiting acid secretion.

Test No. VIII: Activity of promoting the curing of wound

Wister male rats, 10 in each group, were used as experimental animals.

The rats were anaethesized with each ether, and a longitudinally running incised wound, 5 cm in length, was made along the medial line of the back. The wound was closed by four metal clips space at 1 cm intervals. Beginning on the next day, each of the test compounds was orally administered in a dosage of 300 mg/kg twice every day. Five days later, the rats were killed with either, and a skin pieces having three wounds at the center was cut out from each rat. One end of the skin piece was fixed, and a load was exerted on the other end. The weight (tensile strength) required for the tearing of the wounded site of the skin piece was measured.

The results are shown in Table G.

Table G

| Test compound | Tensile strength (g/cm) |
|---|---|
| Control | 158.9 ± 12.1 |
| No. 3 | 233.3 ± 7.9 |
| No. 17 | 211.8 ± 5.9 |
| MMSC (comparison) | 139.7 ± 8.3 |

It can be seen from the results shown in Table G that the compounds of this invention have an action of promoting the curing of wound.

Test No. IX: Anti-allegic activity

Wister male rats, 10 in each group, were used as experimental animals.

The rats were intraperitoneally administered with 5 ml of anti-ovoalbumin diluted with mouse serum to 50 times. Two hours later, 5 ml of a Tyrod's solution containing 2 mg of egg-white albumin and 25 units of heparin was intraperitoneally administered. Five minutes later, the head of each rat was cut off, and the rats were allowed to bleed to death. Thus, the ascites were collected. The ascites were centrifuged at 200 G for 5 minutes. Histamine in the supernatant liquid and the precipitate was determined by a fluorescent method, and according to the following equation, the ratio of histamine freed was calculated.

Each of the test compounds was intraperitoneally administered 1 minute before the application of the antigen. The results are shown in Table H.

$$\text{Ratio of histamine freed (\%)} = \frac{\text{Amount of histamine in the supernatant liquid}}{\text{Amount of histamine in the precipitate + amount of histamine in the supernatant liquid}} \times 100$$

Table H

| Test compound | Dosage (mg/kg, i.p.) | Ratio of histamine freed (%) | Percent inhibition (%) |
|---|---|---|---|
| Control | — | 38.2 | — |
| No. 3 | 30 | 22.7 | 40.6 |
| No. 14 | 30 | 23.5 | 38.5 |
| MMSC (comparison) | 30 | 24.7 | 35.3 |

EXAMPLE OF FORMULATION

Several examples of the formulation of the ulcer treating composition of this invention are shown below. These compositions can be produced by ordinary methods.

| | |
|---|---|
| 1. Tablets | Amount per tablet |
| N-benzoylmethylmethioninesulfonium chloride | 25 mg |
| Sodium bicarbonate | 250 mg |
| Neosilin | 100 mg |
| 2. Powder | Amount per gram |
| N-4-methylbenzoylmethylmethioninesulfonium chloride | 50 mg |
| Neosilin | 400 mg |
| Calcium carbonate | 200 mg |
| Magnesium carbonate | 150 mg |
| 3. Granule | Amount per gram |
| N-4-methoxybenzoylmethylmethioninesulfonium chloride | 250 mg |
| 4. Injecting preparation | |
| N-4-methoxybenzoyl MMSC | 150 mg/ampoule |
| Distilled water for injecting preparations | 2 ml |
| 5. Injecting preparation for intravenous administration | |
| N-benzoyl MMSC | 500 mg/ampoule |
| In use, it is dissolved in 20 ml of a 20% glucose injecting preparation. | |

What we claim is:

1. An ulcer treating composition composed of (1) an antiulceratively effective amount of a methylmethioninesulfonium compound of the formula

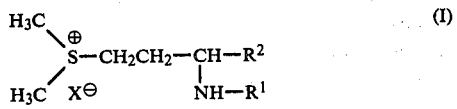

wherein $X^\ominus$ represents an anion;

$R^1$ represents an acyl group of the formula $-COR^3$ in which $R^3$ represents the group

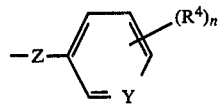

in which Z represents a direct bond, Y represents C, $R^4$ represents a member selected from the class consisting of a hydrogen atom, lower alkyl groups, lower alkoxy groups, di-lower-alkylamino groups and a sulfamoyl group, n is a number of 1 to 3, and two or more $R^4$ groups may be identical or different; and $R^2$ represents the group $-COOR^5$ in which $R^5$ represents a hydrogen atom, an alkyl group with 1 to 5 carbon atoms or a metal- or metal complex-forming moiety, or the group

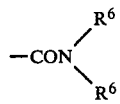

in which $R^6$ groups may be identical or different, and each represent a hydrogen atom or an alkyl group with 1 to 5 carbon atoms.

2. The composition of claim 1 wherein the methylmethioninesulfonium compound is a compound of the following formula

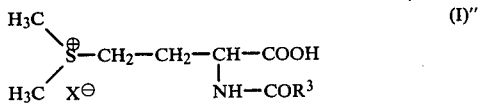

wherein $X^\ominus$ and $R^3$ are as defined with regard to formula (I).

3. The compound according to claim 1 wherein $R^4=3,4$ and $5-OCH_3$, $n=3$, $R^2=COOR^5$, $R^5$=hydrogen and $X^\ominus=Cl$.

4. The compound according to claim 1 wherein $R^4=4-OCH_3$, $n=1$, $R^2=COOR^5$, $R^5$=hydrogen and $X^\ominus=Cl$.

5. The compound according to claim 1 wherein $R^4=2-OCH_3$, $n=1$, $R^2=COOR^5$, $R^5$=hydrogen and $X^\ominus=Cl$.

6. The compound according to claim 1 wherein $R^4=2-OCH_3$ and $5-SO_2NH_2$, $n=2$, $R^2=COOR^5$, $R^5$=hydrogen and $X^\ominus=Cl$.

7. The compound according to claim 1 wherein $R^4=4-N(CH_3)_2$, $n=1$, $R^2=COOR^5$, $R^5$=hydrogen and $X^\ominus=Cl$.

8. The compound according to claim 1 wherein $R^4$=hydrogen, $R^2=COOR^5$, $R^5=Al_3(OH)_4$ and $X^\ominus=Cl$.

9. A method for treating an ulcer, which comprises administering a methylmethioninesulfonium compound to an animal or a human suffering from ulcer in a dosage of about 10 to about 1,000 mg/day/kg of body weight, said methylmethioninesulfonium compound being expressed by the formula

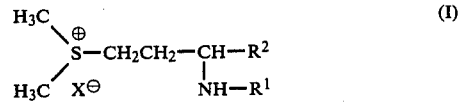

wherein $X^\ominus$ represents an anion;

$R^1$ represents an acyl group of the formula $-COR^3$ in which $R^3$ represents the group

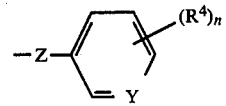

in which Z represents a direct bond, Y represents C, $R^4$ represents a member selected from the class consisting of a hydrogen atom, lower alkyl groups, lower alkoxy groups, di-lower-alkylamino groups and a sulfamoyl group, n is a number of 1 to 3, and two or more $R^4$ groups may be identical or different; and $R^2$ represents the group $-COOR^5$ in which $R^5$ represents a hydrogen atom, an alkyl group with 1 to 5 carbon atoms or a metal- or metal complex-forming moiety, or the group

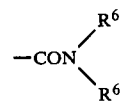

in which $R^6$ groups may be identical or different, and each represent a hydrogen atom or an alkyl group with 1 to 5 carbon atoms.

10. The method according to claim 9 wherein $R^4=3,4$ and $5-OCH_3$, $n=3$, $R^2=COOR^5$, $R^5$=hydrogen and $X^\ominus Cl$.

11. The method according to claim 9 wherein $R^4=4-OCH_3$, $n=1$, $R^2=COOR^5$, $R^5$=hydrogen and $X^\ominus=Cl$.

12. The method according to claim 9 wherein $R^4=2-OCH_3$, $n=1$, $R^2=COOR^5$, $R^5$=hydrogen and $X^\ominus=Cl$.

13. The method according to claim 9 wherein $R^4=2-OCH_3$ and $5-SO_2NH_2$, $n=2$, $R^2=COOR^5$, $R^5$=hydrogen and $X^\ominus=Cl$.

14. The method according to claim 9 wherein $R^4=4-N(CH_3)_2$, $n=1$, $R^2=COOR^5$, $R^5$=hydrogen and $X^\ominus=Cl$.

15. The method according to claim 9 wherein $R^4$=hydrogen, $R^2=COOR^5$, $R^5=Al_3(OH)_4$ and $X^\ominus=Cl$.

* * * * *